United States Patent
Hisamatsu et al.

(10) Patent No.: US 7,252,835 B2
(45) Date of Patent: Aug. 7, 2007

(54) AGENT FOR PREVENTING AND/OR TREATING SINUSITIS

(75) Inventors: KenIchi Hisamatsu, Ibaraki (JP); Keisuke Masuyama, Kumamoto (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 66 days.

(21) Appl. No.: 11/106,662

(22) Filed: Apr. 15, 2005

(65) Prior Publication Data

US 2005/0182115 A1  Aug. 18, 2005

Related U.S. Application Data

(60) Continuation of application No. 10/195,523, filed on Jul. 16, 2002, now abandoned, which is a division of application No. 09/806,159, filed as application No. PCT/JP99/05327 on Sep. 29, 1999.

(30) Foreign Application Priority Data

Sep. 30, 1998 (JP) ............................. P. 10-277094

(51) Int. Cl.
*A61F 13/00* (2006.01)
(52) U.S. Cl. ..................................... 424/434
(58) Field of Classification Search ................. 424/400
See application file for complete search history.

(56) References Cited

U.S. PATENT DOCUMENTS 6,194,431 B1 * 2/2001 Rubin 6,423,721 B1 * 7/2002 Harris et al.

FOREIGN PATENT DOCUMENTS

EP         0641569 A1      3/1995
WO         WO 99/32125     7/1999

OTHER PUBLICATIONS

Manabu Fujita et al., "Effects of a Specific Cysteinyl Leukotriene Antagonist, Pranlukast, on Antigen-induced Cysteinyl Leukotriene-Mediated Rhinitis in Guinea Pigs", Jpn. J. Pharmacol., vol. 75, No. 4, (1997), pp. 347-353.*

(Continued)

*Primary Examiner*—Humera N Sheikh
(74) *Attorney, Agent, or Firm*—Sughrue Mion, PLLC

(57) ABSTRACT

An agent for preventing and/or treating sinusitis, comprising, as an active ingredient, a compound of the formula (I):

(I)

[chemical structure]

or a salt and/or hydrate thereof.

The pranlukast hydrate is useful as an agent for preventing and/or treating sinusitis.

11 Claims, 1 Drawing Sheet

INHIBITORY EFFECT OF PRANLUKAST HYDRATE ON REDUCTION
OF PARANASAL CILIARY MOVEMENT INDUCED BY LTS (LTD$_4$, LTC$_4$)

INVENTION:
$10^{-7}$ M LTD$_4$ + $10^{-6}$ M PRANLUKAST HYDRATE

COMPARISON: $10^{-7}$ M LTD$_4$ **

CONTROL

INVENTION:
$10^{-7}$ M LTC$_4$ + $10^{-6}$ M PRANLUKAST HYDRATE

COMPARISON: $10^{-7}$ M LTC$_4$ **

CONTROL

CILIARY ACTIVITY (%)

OTHER PUBLICATIONS

Taber's Cyclopedic Medical Dictionary, Definition of Sinusitis, p. 1804 (1993).*

Kukhta, A.L. et al., "Leukotriene (LT) Pathway Modifiers: Are They the Newest Line of Therapy for Chronic Sinusitis?: Case Reports", Journal of Allergy and Clinical Immunology, vol. 101, No. 1/2, p. S252, Abstract (Jan. 1998).

Chambers, R.J. et al., "Development of New Chromanol Antagonists of Leukotriene $D_4$", Bioorganic & Medicinal Chemistry Letters, vol. 8, No. 14, 1791-1796, (Jul. 21, 1998).

Shoji Yamazaki et al., "Effects of thrombotic acid A2 and histamine on allergic rhinitis in guinea pigs," Jpn. Pharmacol. Ther. (Medicine and Treatment), vol. 26, No. 8 (Aug. 20, 1998), pp. 1217-1227.

Manabu Fujita et al., "Immediate phase and delayed phase effects of pranlukast hydrate on antigen evoked nasal allergy model in guinea pigs," Jpn. Pharmacol Ther. (Medicine and Treatment, vol. 25, No. 5, (1997), pp. 1379-1386.

S. Narita et al., "Effects of a cysteinyl leukotriene antagonist, ONO-1078 (pranlukast), on total airway resistance after antigen challenge in sensitized guinea pigs," Inflamm. Res., vol. 46, No. 4 (1997), pp. 143-146.

Manabu Fujita et al., "Effects of a Specific Cysteinyl Leukotriene Antagonist, Prankukast, on Antigen-Induced Cysteinyl Leukotrience-Mediated Rhinitis in Guinea Pigs," Jpn. J. Pharmacol., vol. 75, No. 4, (1997), pp. 347-353.

F. Takahisa et al. edit, "Merck Manual, 16th edition," (May 1, 1995, 3rd printing), Chapter "Sinusitis", pp. 2243-2244.

American Academy of Allergy Asthma and Immunology 54th Annual Meeting, Washington, D.C., Mar. 13-18, 1998, Abstracts of papers to be presented during scientific sessions.

* cited by examiner

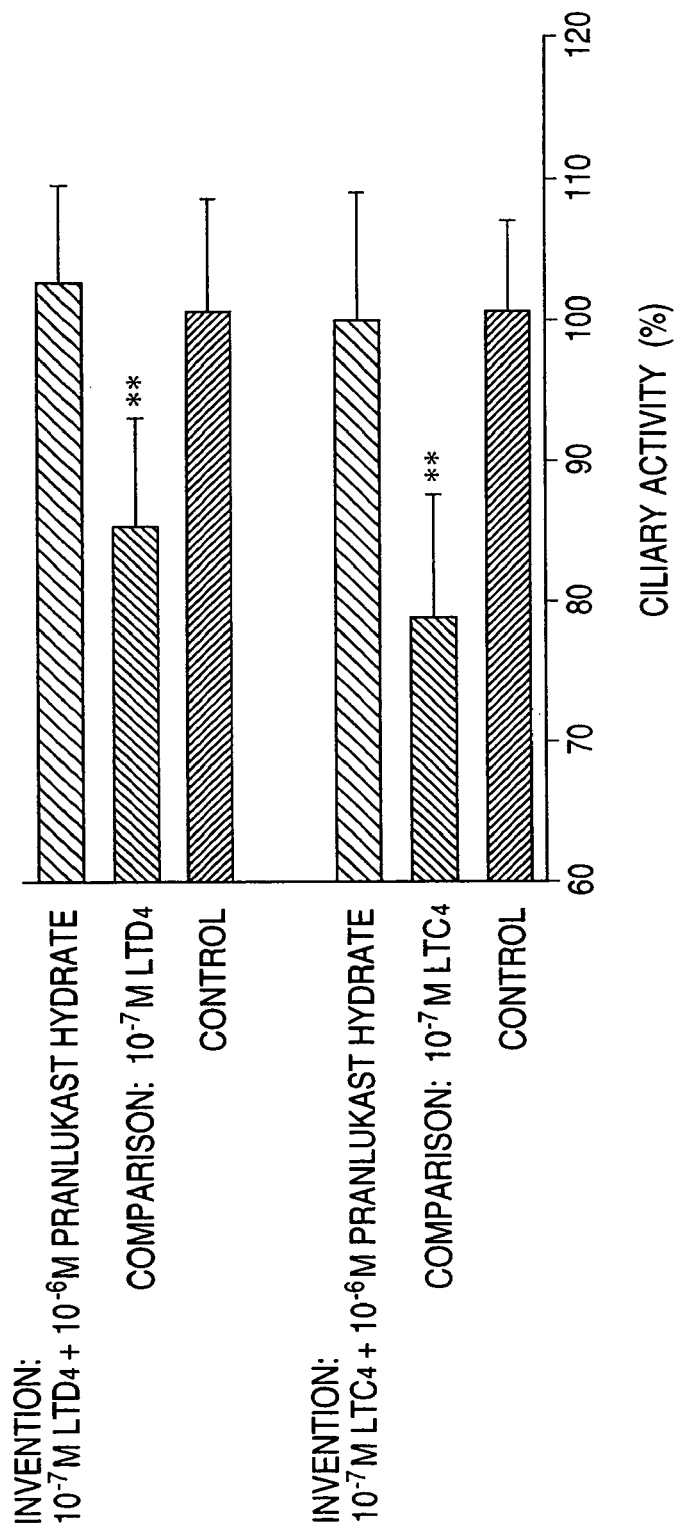

AGENT FOR PREVENTING AND/OR TREATING SINUSITIS

This is a Continuation Application of application Ser. No. 10/195,523 filed Jul. 16, 2002 now abandoned, which is a divisional of application Ser. No. 09/806,159 filed on Mar. 28, 2001 (now abandoned), which is a U.S. National stage application of PCT/JP99/05327, filed Sep. 29, 1999, the entire disclosures of which are incorporated herein by reference.

TECHNICAL FIELD

The present invention relates to an agent for preventing and/or treating sinusitis, comprising, as an active ingredient, a compound of the formula (I):

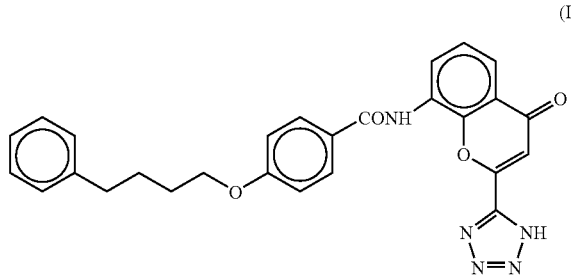

or a salt and/or hydrate thereof.

BACKGROUND ART

Sinusitis is an inflammation of paranasal sinus mucosa and is a disease, and its chief complaints are rhinorrhea, nasal obstruction and postnasal discharge.

The paranasal sinus mucosa has a mucus cilium transportation mechanism and takes charge of a defense mechanism in the living body by physiologically transporting and discharging foreign bodies together with mucus. It is considered that accumulation of inflammation products occurs in the paranasal sinus when ciliary movement is injured and prolongation and chronicity of inflammation are induced.

It is known that LTs ($LTC_4$, $LTD_4$, $LTE_4$) are frequently detected in the nasal flow of chronic sinusitis patients (*Gendai Iryo*, 19: 3041 (1987)). Among these, with regard to $LTC_4$, there are reports that it inhibits ciliary movement (*Clin. Allergy*, 17: 95-103 (1987) and *Clin. Exp. Allergy*, 20: 389-393, (1990)), while there are reports that it accelerates the movement for a short time (*J. Allergy Clin. Immunol.*, 72: 663-667 (1983) and *Acta. Physiol. Scand*, 141: 415-420 (1991)). Also, it is reported that $LTD_4$ inhibits ciliary movement but $LTE_4$ exerts less influence upon ciliary movement (*Am. J. Physiol., Vol.* 271, No. 2(1), III, L216-L224 (1996)).

It is known that a compound of the formula (I) or a salt and/or hydrate thereof has an anti-allergy activity based on SRS ($LTC_4$, $LTD_4$, $LTE_4$) antagonism and is used as an agent for treating asthma and the like (EP-A-0173516). Furthermore, this compound is also known as an agent for treating itching (WO 93/17709).

DISCLOSURE OF THE INVENTION

This time, the present inventors found for the first time that a compound of the formula (I) or a salt and/or hydrate thereof is effective for sinusitis, and thus the present invention has been accomplished. Particularly, it was found that 4-oxo-8-[4-(4-phenylbutoxy)benzoylamino]-2-(tetrazol-5-yl)4H-1-benzopyran·½ hydrate (common name: pranlukast hydrate; hereinafter referred to as the "pranlukast hydrate") represented by the formula:

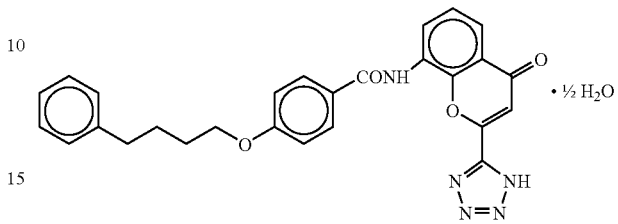

inhibits reduction of paranasal sinus ciliary movement induced by LTs, it was further found that pranlukast hydrate is also clinically effective for the improvement of symptoms and findings of sinusitis patients, and thus the present invention has been accomplished.

Since effectiveness of a compound of the formula (I) or a salt and/or hydrate thereof on sinusitis has not been examined clinically until now, it was completely unknown. This time, the effectiveness was confirmed for the first time.

The present invention relates to an agent for preventing and/or treating sinusitis, comprising, as an active ingredient, a compound of the formula (I):

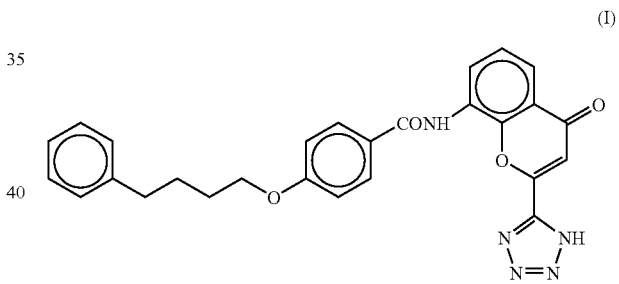

or a salt and/or hydrate thereof. A preferred active ingredient is pranlukast hydrate, namely 4-oxo-8-[4-(4-phenylbutoxy)benzoylamino]-2-(tetrazol-5-yl )4H-1-benzopyran·½ represented by the formula:

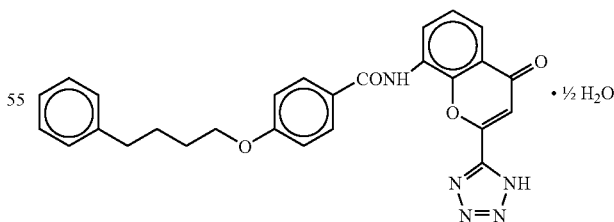

BRIEF DESCRIPTION OF THE DRAWINGS

FIG. 1 is a graph showing the inhibitory effect of pranlukast hydrate on the reduction of paranasal sinus mucosa ciliary activity induced by LTs ($LTD_4$, $LTC_4$).

PRODUCTION METHOD

The compound of the formula (I) or a salt and/or hydrate thereof can be produced by the method described in the specification of EP-A-0173516 or other known method.

Pharmacological Activity:

Since the compound of the formula (I) or a salt and/or hydrate thereof shows an inhibitory action on the reduction of paranasal sinus mucosa ciliary activity induced by LTs and improves various symptoms and findings of sinusitis, it is useful as an agent for preventing and/or treating sinusitis.

Toxicity:

It was confirmed that the compound of the formula (I) or a salt and/or hydrate thereof has sufficiently low toxicity and is sufficiently safe for using it as a medicament. For example, as the acute toxicity of pranlukast hydrate, its minimum lethal dose was 2,000 mg/kg or more (oral or subcutaneous administration), or 30 mg/kg or more (intravenous injection) in mice and rats (both males and females).

Application to Medicament:

For the purpose above described, the compound of the formula (I) or a salt and/or hydrate thereof may be normally administered systemically by oral, subcutaneous or intravenous administration or locally by intranasal administration.

The doses to be administered are determined depending upon age, body weight, symptom, the desired therapeutic effect, the route of administration, and the duration of the treatment etc. In the human adult, the doses per person per dose are generally between 100 mg and 300 mg, by oral administration, up to several times per day, and between 1 mg and 50 mg, by subcutaneous, intravenous or intranasal administration up to several times per day, or by continuous administration between 1 and 24 hrs. per day into vein.

As mentioned above, the doses to be used depend upon various conditions. Therefore, there are cases in which doses lower than or greater than the ranges specified above may be used.

The compound of the formula (I) or a salt and/or hydrate thereof may be administered as inner solid compositions or inner liquid compositions for oral administration, as injections for subcutaneous or intravenous administration (including continuous infusion into vein) or as external compositions for intranasal administration.

Inner solid compositions for oral administration include compressed tablets, pills, capsules, dispersible powders and granules etc. Capsules contain hard capsules and soft capsules.

In such inner solid compositions, the compound of the formula (I) or a salt and/or hydrate thereof is admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, aspartic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, suspensions, emulsions, syrups and elixirs etc. In such liquid compositions, the compound of the formula (I) or a salt and/or hydrate thereof is comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavouring agents, perfuming agents, preserving agents and buffer agents etc.

Injections for subcutaneous or intravenous administration (including continuous infusion into vein) include solutions, suspensions, emulsions, and solid injections which are used by dissolving or suspending in a solvent when used. The compound of the formula (I) or a salt and/or hydrate thereof is used by dissolving, suspending or emulsifying it in a solvent. Examples of the solvent include a distilled water for injection, a physiological saline, a buffer (phosphate buffer, or the like), plant oil, propylene glycol, polyethylene glycol and alcohol such as ethanol etc. and a combination thereof. Such compositions may comprise additional diluents: e.g. stabilizing agent, assisting agents for dissolving (glutamic acid, aspartic acid, POLYSOLBATE80 (registered trade mark) etc), suspending agent, emulsifying agents, buffer agents and preserve agents etc. They may be sterilized for example, by filtration through a bacteria-retaining filter, by incorporation of sterilizing agents in the compositions or by irradiation. They may also be manufactured in the form of sterile solid compositions such as freezed-dry solid and which can be dissolved in sterile water or some other sterile diluent for injection immediately before use.

External compositions for intranasal administration include liquids for external use. Such liquids for external use include solutions, suspensions, emulsions and solid injections which are used by dissolving or suspending in a solvent when used. The compound of the formula (I) or a salt and/or hydrate thereof is used by dissolving, suspending or emulsifying it in a solvent. Examples of the solvent include a physiological saline, a buffer (phosphate buffer, or the like), propylene glycol, polyethylene glycol, and the like, and a combination thereof. These liquids for external use can further contain stabilizing agents, assisting agents for dissolving (glutamic acid, aspartic acid, or the like), suspending agents (POLYSORBATE80 (trade name), or a viscosity-providing polymer such as carboxymethylcellulose or polyvinyl alcohol), emulsifying agents, buffer, preservative, and the like.

BEST MODE FOR CARRYING OUT THE INVENTION

The present invention is explained in detail based on examples (Test Examples and Formulation Examples); however, the present invention is not limited to them.

TEST EXAMPLE 1

Inhibitory Effect of Pranlukast Hydrate on the Reduction of Ciliary Movement in Paranasal Sinus Mucosa Induced by LTs 1) Culturing of Paranasal Sinus Mucosa Normal human paranasal sinus mucosa obtained at the time of surgical operation of facial trauma or the like was used on the agreement of the patient. The collected paranasal sinus mucosa was thoroughly washed with a culture medium RPMI 1640 (Gibco Life Technologies), cut into 4 mm×4 mm species and then subjected to tissue culture in a culturing chamber of 35 mm×10 mm using RPMI 1640 containing 10% FCS (fetal calf serum). In order to remove mucus and cellular debris, the culture medium was exchanged every other day.

2) Preparation of Test Solutions

Each of $LTD_4$ and $LTC_4$ (Ultrafine Chemicals, England) was dissolved into 20% ethanol to prepare 100 μM solution and then diluted with RPMI 1640 to a concentration of 0.1 μM. Pranlukast hydrate was prepared to the final concentration of 1 μM.

3) Observation of Mucosa Epithelial Cells and Measurement of Ciliary Activity

The surface of paranasal sinus mucosa in a chamber was observed under an inverted phase contrast microscope at 37° C. under 5% $CO_2$, and ciliary activity of cells which was displayed on a TV monitor with magnifying about 2,500 times was measured photoelectrically using photosensor. When a test solution was added to the mucosal tissue, culture medium in the chamber was removed and mucosal tissue was washed with RPMI 1640 and then the test solution (1 ml) was injected. As a control, the ciliary activity was measured in case of injecting only RPMI 1640 into the chamber. By defining the ciliary activity measured just before injection of each test solution (0 minute) as the reference value (100), the ciliary activity measured after injection of each test solution was expressed as percentage (%) of the reference value. The ciliary activity measured after 4 hours of the injection of each test solution in the case of $LTD_4$, or after 6 hours of the injection of each test solution in the case of $LTC_4$ was employed. The results are shown in FIG. 1. In FIG. 1, each value indicates average and standard deviation, and ** indicates the presence of a significant difference of $p<0.01$ from the control group (n=10).

It was indicated from the results shown in FIG. 1 that pranlukast hydrate (1 μM) has the activity to inhibit reduction of paranasal sinus mucosa ciliary activity induced by $LTD_4$ or $LTC_4$ (each 0.1 μM).

TEST EXAMPLE 2

Effect of Pranlukast Hydrate on Intractable Sinusitis

Pranlukast hydrate was orally administered to intractable sinusitis patients (34 persons, average age 54.4 years) at a daily dose of 450 mg (112.5 mg/capsule, 2 capsules per 1 time, twice a day (after every breakfast and supper), every day administration). On the 2 weeks, 4 weeks, 6 weeks and 8 weeks after the administration, 1) improving degree of the nasal mucosa swelling, 2) improving degree of the properties of nasal flow, 3) improving degree of the amount of nasal flow, 4) improving degree of the postnasal discharge, 5) improving degree of the nasal obstruction, 6) improving degree of the nasal flow (frequency of blowing nose) and 7) improving degree of the X-ray shadow of each patient were judged (however, parameters in respective weeks are not constant). The results were evaluated by four steps in terms of significantly improved, improved, unchanged and worsened, and improved or more (significantly improved and improved) was judged as effective and its ratio (%) was calculated. The results are shown in Tables 1 to 7.

TABLE 1

Improving degree of the nasal mucosa swelling in intractable sinusitis by pranlukast hydrate

| Administration days | Effective ratio (%) |
|---|---|
| On the 2nd week | 32% |
| On the 4th week | 29% |
| On the 6th week | 43% |
| On the 8th week | 40% |

TABLE 2

Improving degree of the properties of nasal flow in intractable sinusitis by pranlukast hydrate

| Administration days | Effective ratio (%) |
|---|---|
| On the 2nd week | 33% |
| On the 4th week | 48% |
| On the 6th week | 52% |
| On the 8th week | 53% |

TABLE 3

Improving degree of the amount of nasal flow in intractable sinusitis by pranlukast hydrate

| Administration days | Effective ratio (%) |
|---|---|
| On the 2nd week | 52% |
| On the 4th week | 55% |
| On the 6th week | 68% |
| On the 8th week | 65% |

TABLE 4

Improving degree of the postnasal discharge in intractable sinusitis by pranlukast hydrate

| Administration days | Effective ratio (%) |
|---|---|
| On the 2nd week | 39% |
| On the 4th week | 38% |
| On the 6th week | 39% |
| On the 8th week | 62% |

TABLE 5

Improving degree of the nasal obstruction in intractable sinusitis by pranlukast hydrate

| Administration days | Effective ratio (%) |
|---|---|
| On the 2nd week | 19% |
| On the 4th week | 21% |
| On the 6th week | 35% |
| On the 8th week | 29% |

TABLE 6

Improving degree of the nasal flow (frequency of blowing nose) in intractable sinusitis by pranlukast hydrate

| Administration days | Effective ratio (%) |
|---|---|
| On the 2nd week | 34% |
| On the 4th week | 52% |

TABLE 6-continued

Improving degree of the nasal flow (frequency of blowing nose) in intractable sinusitis by pranlukast hydrate

| Administration days | Effective ratio (%) |
| --- | --- |
| On the 6th week | 65% |
| On the 8th week | 60% |

TABLE 7

Improving degree of the X-ray shadow in intractable sinusitis by pranlukast hydrate

| Administration days | Effective ratio (%) |
| --- | --- |
| On the 8th week | 83% |

It was found from the results shown in Tables 1 to 7 that pranlukast hydrate improves various subjective symptoms (postnatal discharge, nasal obstruction and nasal flow (frequency of blowing nose)) and objective findings (nasal mucosa swelling, properties of nasal flow, amount of nasal flow and X-ray shadow) of intractable sinusitis and therefore has clinical effects on sinusitis.

FORMULATION EXAMPLE 1

The following respective components were mixed in the usual way and then packed in gelatin capsules to obtain capsules.

| Pranlukast hydrate | 112.5 mg |
| --- | --- |
| Lactose | 52.5 mg |
| Magnesium stearate | suitable amount |
| Hydroxypropylcellulose | suitable amount |

The invention claimed is:

1. A method for treating sinusitis, comprising administering a composition comprising a pharmacologically effective amount of an active ingredient to a patient in need thereof, said active ingredient consisting of a compound of the formula (I):

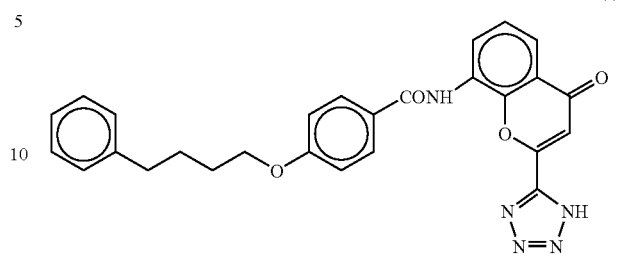

or a salt and/or hydrate thereof.

2. The method for treating sinusitis according to claim 1, wherein the active ingredient is 4-oxo-8-[4-(4-phenylbutoxy)benzoylamino]-2-(tetrazol-5-yl)-4H-1-benzopyran hemihydrate.

3. The method for treating sinusitis according to claim 1, which improves nasal mucosa swelling.

4. The method for treating sinusitis according to claim 1, which improves properties of nasal flow.

5. The method for treating sinusitis according to claim 1, which improves the amount of nasal flow.

6. The method for treating sinusitis according to claim 1, which improves postnasal discharge.

7. The method for treating sinusitis according to claim 1, which improves nasal obstruction.

8. The method for treating sinusitis according to claim 1, which improves frequency of blowing nose.

9. The method for treating sinusitis according to claim 1, which improves X-ray shadow.

10. The method according to any one of claims 2 to 9, characterized by administering to a human 450 mg of 4-oxo-8-[4-(4-phenylbutoxy)benzoylamino]-2-(tetrazol-5-yl)-4H-1-benzopyran hemihydrate per day as an active ingredient.

11. The method according to any one of claims 2 to 9, characterized by administering to a human 225 mg of 4-oxo-8-[4-(4-phenylbutoxy)benzoylamino]-2-(tetrazol-5-yl)-4H-1-benzopyran hemihydrate twice a day as an active ingredient.

\* \* \* \* \*